United States Patent
Reddy et al.

(10) Patent No.: US 7,790,886 B2
(45) Date of Patent: Sep. 7, 2010

(54) POLYMORPHIC FORMS OF ZIPRASIDONE AND ITS HYDROCHLORIDE SALT AND PROCESS FOR PREPARATION THEREOF

(75) Inventors: Manne Satyanarayana Reddy, Hyderabad (IN); Thirumalai Rajan Srinivasan, Hyderabad (IN); Venka Bhaskara Rao Uppala, Hyderabad (IN); Mummadi Venkatesh, Hyderabad (IN); Akundi Surya Prabhakar, Hyderabad (IN)

(73) Assignees: Dr. Reddy's Laboratories, Inc., Bridgewater, NJ (US); Dr. Reddy's Laboratories Limited, Hyderabad (IN)

( * ) Notice: Subject to any disclaimer, the term of this patent is extended or adjusted under 35 U.S.C. 154(b) by 0 days.

(21) Appl. No.: 12/348,360

(22) Filed: Jan. 5, 2009

(65) Prior Publication Data
US 2009/0137605 A1 May 28, 2009

Related U.S. Application Data

(62) Division of application No. 10/729,837, filed on Dec. 4, 2003, now Pat. No. 7,488,729.

(30) Foreign Application Priority Data
Dec. 4, 2002 (IN) .......................... 907/MAS/2002

(51) Int. Cl.
*C07D 409/14* (2006.01)
(52) U.S. Cl. ..................................... 544/368
(58) Field of Classification Search ....................... None
See application file for complete search history.

(56) References Cited

U.S. PATENT DOCUMENTS 4,831,031 A * 5/1989 Lowe et al. ............. 514/254.02
6,150,366 A 11/2000 Arenson et al.

FOREIGN PATENT DOCUMENTS

| EP | 0584903 A1 | 3/1994 |
|---|---|---|
| EP | 0586191 A1 | 3/1994 |
| EP | 0965343 A2 | 12/1999 |
| EP | 1157726 A1 | 11/2001 |
| WO | 95/00510 A1 | 1/1995 |
| WO | 97/42190 A1 | 11/1997 |
| WO | 00/59489 A2 | 10/2000 |
| WO | 03/063833 A1 | 8/2003 |
| WO | 03/070246 A1 | 8/2003 |

OTHER PUBLICATIONS

Howard, H. R., et al., "3-Benzisothiazolylpiperazine Derivatives as Potential Atypical Antipsychotic Agents," Journal of Medicinal Chemistry, 1996, vol. 39, pp. 143-148.
Lieberman, Herbert A., ed. "Pharmaceutical Dosage Forms: Tablets," vol. 2 (1989), pp. 462-465.

* cited by examiner

*Primary Examiner*—Kamal A Saeed
(74) *Attorney, Agent, or Firm*—Robert A. Franks; Lee C. Banks; Anjum Swaroop

(57) ABSTRACT

The present invention is related to crystalline forms of ziprasidone and its hydrochloride salt and an amorphous form of ziprasidone hydrochloride and the process for the preparation thereof. The crystalline forms and amorphous form of the invention are suitable for pharmaceutical purposes in the treatment of psychosis. The processes of the invention are simple, non-hazardous and commercially suitable.

12 Claims, 2 Drawing Sheets

POLYMORPHIC FORMS OF ZIPRASIDONE AND ITS HYDROCHLORIDE SALT AND PROCESS FOR PREPARATION THEREOF

CROSS-REFERENCE TO RELATED APPLICATION

This application claims priority of Indian Patent Application No. 907/MAS/2002, filed Dec. 4, 2002, the disclosure of which is incorporated herein by reference in its entirety.

FIELD OF THE INVENTION

The present invention relates to new amorphous form of ziprasidone hydrochloride and crystalline forms of ziprasidone and its hydrochloride salt, processes for preparation thereof, and compositions containing the amorphous and crystalline forms.

The present invention also relates to a method of treating a psychosis, comprising administering to a patient in need of such treatment an effective amount of amorphous form of ziprasidone hydrochloride or crystalline forms of ziprasidone or its hydrochloride salt

BACKGROUND OF THE INVENTION

Ziprasidone, 5-(2-(4-(1,2-benzisothiozole-3yl)-1-piperazinyl)ethyl)-6-chloro-1,3-dihydro-2H-indole-2-one is an anti psychotic agent that is used for the treatment of psychotic disorders of the schizophrenic types, and is also useful for removing or ameliorating such symptoms as anxiety, agitation, excessive aggression, tension and social or emotional withdrawal in psychotic patients.

It is known that polymorphic forms of the same drug may have substantial differences in certain pharmaceutically important properties. Therefore, there is a continuing need for new solid forms of ziprasidone and its salts and new methods of preparation.

SUMMARY OF THE INVENTION

The invention relates to an amorphous form of ziprasidone hydrochloride. Preferably, the amorphous form of ziprasidone hydrochloride may have substantially the same X-ray diffraction pattern as shown in FIG. 1. Various embodiments and variants are provided.

The invention also relates to a composition that comprises ziprasidone hydrochloride in a solid form, wherein at least 80% by weight of the solid ziprasidone hydrochloride is an amorphous form of ziprasidone hydrochloride.

The invention also relates to a process for preparation of amorphous form of ziprasidone hydrochloride by converting ziprasidone to amorphous ziprasidone hydrochloride.

The invention also relates to a pharmaceutical composition that comprises an amorphous form of ziprasidone hydrochloride and one or more pharmaceutically acceptable carriers or diluents. Preferably, the pharmaceutical composition is in a solid dosage form for oral administration, such as a tablet.

The invention also relates to a crystalline form of ziprasidone. Preferably, the crystalline form of ziprasidone has an X-ray diffraction pattern, expressed in terms of 2 theta angles, that includes four or more peaks selected from the group consisting of 16.34±0.009, 12.21±0.009, 25.16±0.009, 27.02±0.009, 24.21±0.009, 5.26±0.009 and 18.51±0.009 degrees. The invention also relates to a pharmaceutical composition having the crystalline form of ziprasidone. Pharmaceutical compositions of the invention may be formulated, for example, as solid dosage forms for oral administration.

The invention also relates to a method of treating a psychosis, comprising administering to a patient in need of such treatment an effective amount of an amorphous form of ziprasidone hydrochloride or crystalline forms of ziprasidone or its hydrochloride salt.

BRIEF DESCRIPTION OF THE ACCOMPANYING DRAWINGS

DETAILED DESCRIPTION OF THE INVENTION

Figure 1:
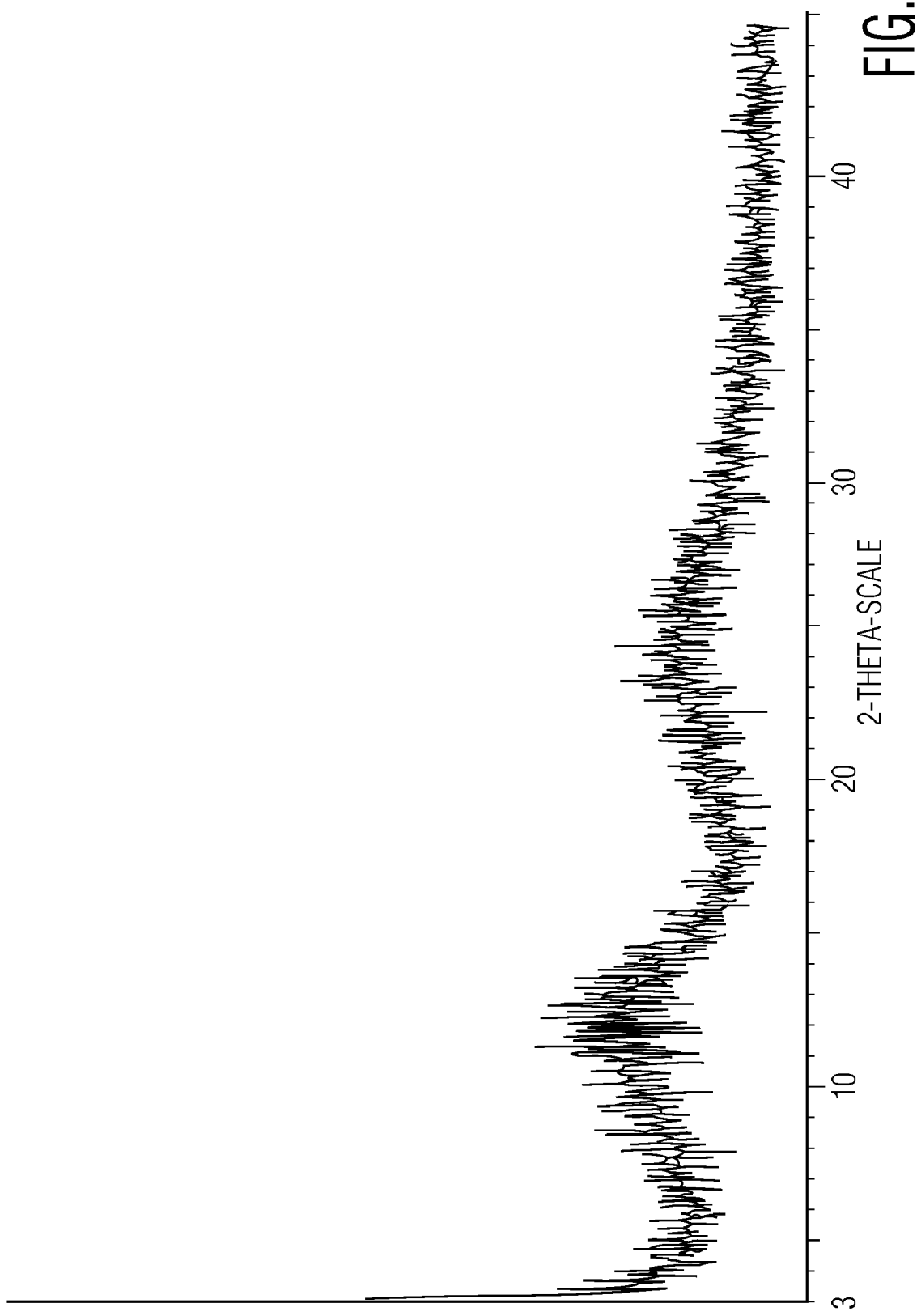
FIG. 1 shows a sample X-ray power diffractogram of an amorphous form of ziprasidone hydrochloride.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Unless stated to the contrary, any use of the words such as "including," "containing," "comprising," "having" and the like, means "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

For purposes of the present invention, the following terms are defined below.

"Pharmaceutically acceptable" means that which is useful in preparing a pharmaceutical composition that is generally non-toxic and is not biologically undesirable and includes that which is acceptable for veterinary use and/or human pharmaceutical use.

The term "composition" includes, but is not limited to, a powder, a suspension, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, additional active ingredient(s), and pharmaceutically acceptable excipients.

The term "excipient" means a component of a pharmaceutical product that is not the active ingredient, such as filler, diluent, carrier, and so on. The excipients that are useful in preparing a pharmaceutical composition are preferably generally safe, non-toxic and neither biologically nor otherwise undesirable, and are acceptable for veterinary use as well as human pharmaceutical use. "A pharmaceutically acceptable excipient" as used in the specification and claims includes both one and more than one such excipient.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction, which produces the indicated and/or the desired product, may not necessarily result directly from the combination of two reagents, which were initially added, i.e., there may be one or more intermediates which are produced in the mixture which ultimately leads to the formation of the indicated and/or the desired product. Also, the term "isolating" is used to indicate separation of the compound being isolated regardless of the purity of the isolated compound from any unwanted substance which presents with the compound as a mixture. Thus, degree of the purity of the isolated or separated compound does not affect the status of "isolating".

The term "substantially free of" in reference to a composition, as used herein, means that said substance cannot be detected in the composition by methods known to those skilled in the art at the time of the filing of this application.

Ziprasidone hydrochloride has the chemical structure,

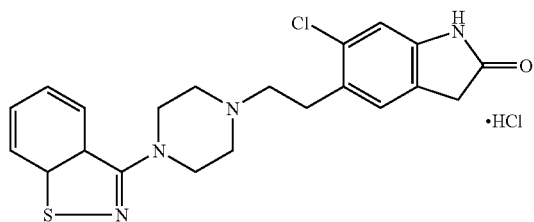

U.S. Pat. No. 5,312,925 discloses mono and hemi hydrated forms and anhydrous form of ziprasidone hydrochloride, which are characterized by X-ray diffractograms and Infrared spectra. The ziprasidone hydrochloride monohydrate crystal form was prepared by treating ziprasidone with aqueous hydrochloric acid at an elevated temperature, followed by controlled drying. For convenience, the crystalline form of ziprasidone hydrochloride monohydrate disclosed in U.S. Pat. No. 5,312,925, herein incorporated by reference, is designated as crystalline Form I.

Different solid forms of the same drug may exhibit different properties, including characteristics that have functional implications with respect to their use as active ingredients of pharmaceutical products. For example, polymorphs of the same drug may have substantial differences in such pharmaceutically important properties as dissolution rates and bioavailability. Likewise, different polymorphs may have different processing properties, such as hydroscopicity, flowability, and the like, which could affect their suitability as active pharmaceuticals for commercial production.

Crystalline ziprasidone hydrochloride may be preferably prepared by making a suspension of ziprasidone in a ketone solvent, such as acetone, diethyl ketone, methyl isobutyl ketone, methyl ethyl ketone or mixtures thereof. Then aqueous hydrochloric acid solution is added to the suspension, and the resulting mixture is heated to an elevated temperature, preferably reflux temperature. The reaction mixture may be heated for 1-24 hours but preferably for 1-2 hours. After the heating, the reaction mixture is cooled preferably to ambient temperature. A solid is formed and may be isolated by any conventional filtering technique. The isolated solid may then be dried at an elevated temperature, preferably between about 50° C. and about 100° C. until a constant weight of the solid is obtained to afford crystalline ziprasidone hydrochloride. The moisture content of crystalline ziprasidone hydrochloride obtained may be between about 3.5 and about 4.5% by weight. The moisture content of the present invention may be measured on Mettler DL-35 instrument using Karl-Fisher reagent.

It is readily understood by one of ordinary skill in the art that the reaction times set forth above may vary depending upon the amount of the reactants used in the process.

Ziprasidone used in the process of the invention may be crude or purified and may be crystalline or amorphous. The ziprasidone itself may be obtained via a condensation of 5-(2-chloroethyl)-6-chloro oxindole and 3-(1-piperazinyl)-1,2-benzisothiazole or via the synthesis described in U.S. Pat. No. 5,338,846, which is herein incorporated by reference or by titrating an acid addition salt of ziprasidone with a base such as, for example, sodium hydroxide or potassium hydroxide.

The invention relates to an amorphous form of ziprasidone hydrochloride. The amorphous form of ziprasidone hydrochloride of the invention can have a moisture content preferably between about 0.5 and about 7.5%, more preferably between about 0.5 and about 4.5% by weight, even more preferably between about 3.5 and about 4.5%, yet further preferably between about 4.0 and about 4.5%.

A particular process for preparation of an amorphous form of ziprasidone hydrochloride is provided and includes: a) providing ziprasidone hydrochloride solution in an aqueous alcoholic solvent; b) removing said solvent, thereby forming a solid mass; and d) isolating said solid mass, which is the amorphous form of ziprasidone hydrochloride. The aqueous alcoholic solvent is a mixture of water and a lower alky alcohol such as an alcoholic solvent such as ethanol, methanol, propanol, t-butanol, n-butanol, isopropanol or mixtures thereof. The solution of ziprasidone hydrochloride may be prepared by directly dissolving solid ziprasidone hydrochloride in an alcoholic solvent or may be prepared by using ziprasidone which is then treated by hydrochloric acid. A particular process for the preparation of ziprasidone hydrochloride solution used in this aspect of the invention may include: a) suspending ziprasidone base in acetic acid; b) adding aqueous hydrochloric acid solution at slightly above the ambient temperature, preferably at about 30-70° C., preferably 40-50° C.; c) adding water and an alcoholic solvent such as ethanol, methanol, propanol, t-butanol, n-butanol, isopropanol or mixtures thereof, and d) heating the reaction mixture to an elevated temperature for 1-24 hours, preferably 1-2 hours.

The elevated temperature may be any temperature that allows a clear solution of the reaction mixture but preferably is reflux temperature.

The removal of the solvent may be done under reduced pressure and the obtained solid cake is then isolated by a conventional technique, which may or may not include washing the solid cake with a fresh cold water or an aqueous alcoholic solvent such as a mixture of water and a lower alkyl alcohol, e.g. ethanol, methanol, propanol, t-butanol, n-butanol, isopropanol or mixtures thereof. The obtained amorphous form of ziprasidone may be dried at an elevated temperature, preferably at about 50° C.-about 100° C.

The amorphous form of ziprasidone hydrochloride produced by this process may be characterized by an X-ray powder diffraction pattern, as for example shown in FIG. 1.

The X-ray diffractograms was measured on Bruker Axe, DS advance Power X-ray Diffractometer with Cu K alpha-1 Radiation source.

The invention also relates to a crystalline form of ziprasidone. The crystalline form of ziprasidone is prepared by a process comprising a) providing a solution of a salt of ziprasidone in an aqueous solvent; b) treating said solution with aqueous basic solution or caustic lye thereby forming a precipitate; and c) isolating the precipitate, which is the crystalline form of ziprasidone.

As a preferred embodiment, the solution of a salt of ziprasidone of the above process may be prepared by a) treating crude or purified ziprasidone with methane sulfonic acid in methanol media where the ziprasidone forms a mesylate salt; and b) dissolving the ziprasidone mesylate salt in water or in a mixture of water and an alcoholic solvent.

The aqueous basic solution is preferably a solution of alkali metal hydroxide in water such as, for example, sodium hydroxide or potassium hydroxide solution.

Figure 2:
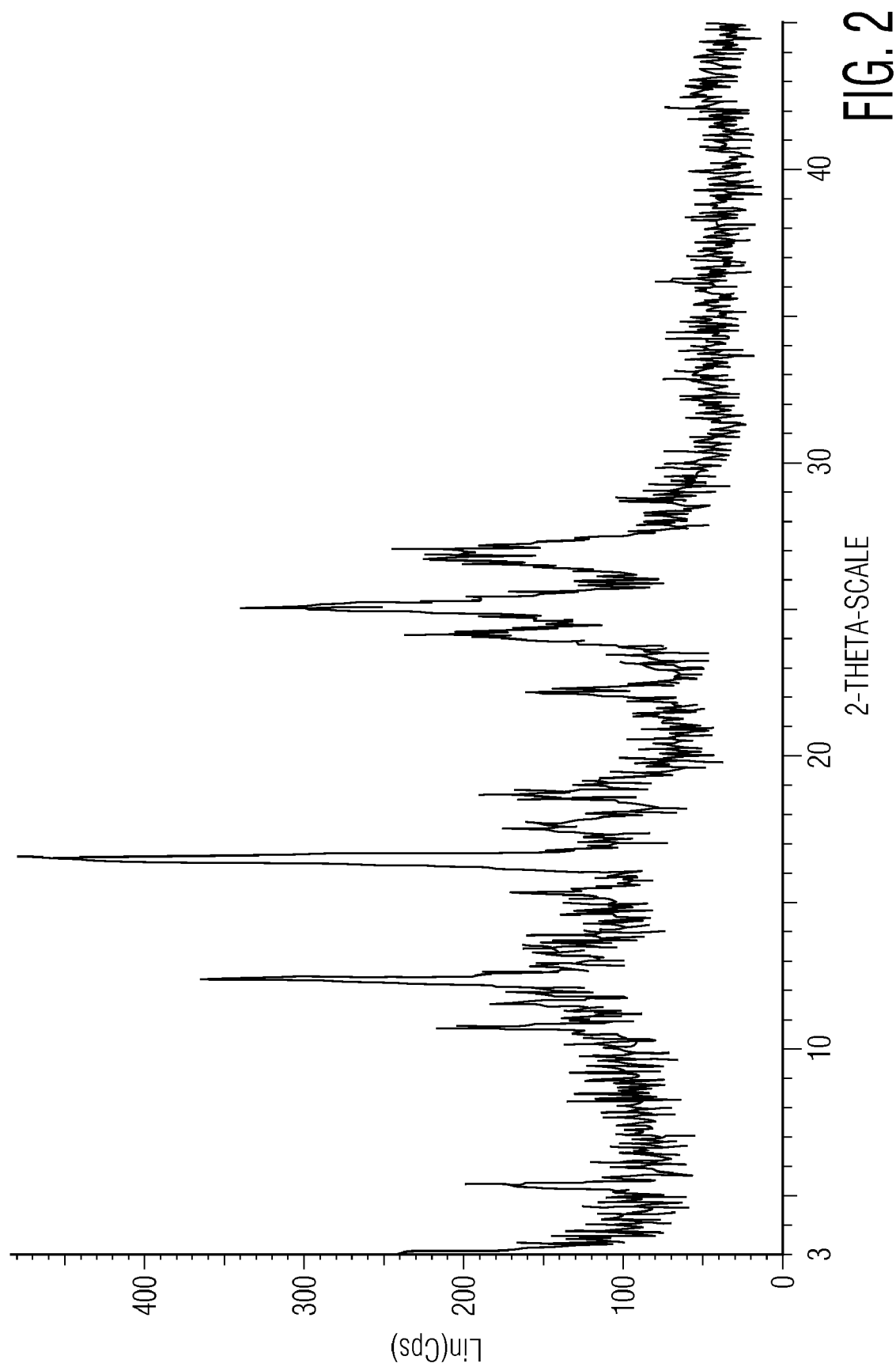
FIG. 2 shows a sample X-ray power diffractogram of a crystalline form of ziprasidone.

An X-ray powder diffraction pattern of the crystalline form of ziprasidone produced via the above process of the invention was obtained as shown in FIG. 2, and the characteristic 2-theta values (in degrees) of the identified peaks in the X-ray diffractogram are 16.335, 12.209, 25.156, 27.019, 24.21, 5.2555 and 18.511. The X-ray diffractograms was measured on Bruker Axe, DS advance Power X-ray Diffractometer with Cu K alpha-1 Radiation source.

It should be kept in mind that slight variations in observed 2 theta angles values are expected based on the specific diffractometer employed, the analyst and the sample preparation technique. More variation is expected for the relative peak intensities. Identification of the exact crystalline form of a compound should be based primarily on observed 2 theta angles with lesser importance attributed to relative peak intensities. The peaks reported herein are listed in order of their peak intensities. Thus, the first listed peak has stronger intensity than the second listed peak in the pattern. 2 theta diffraction angles and corresponding d-spacing values account for positions of various peaks in the X-ray powder diffraction pattern. D-spacing values are calculated with observed 2 theta angles and copper K($\alpha$1) wavelength using the Bragg equation well known to those of skill in the art.

Thus, some margin of error may be present in each of the 2 theta angle assignments reported herein. The assigned margin of error in the 2 theta angles for the crystalline form of ziprasidone is approximately ±0.009 for each of the peak assignments. In view of the assigned margin of error, in a preferred variant, the crystalline form of ziprasidone may be characterized by an X-ray diffraction pattern, expressed in terms of 2 theta angles, that includes four or more peaks selected from the group consisting of 16.34±0.009, 12.21±0.009, 25.16±0.009, 27.02±0.009, 24.21±0.009, 5.26±0.009 and 18.51±0.009 degrees.

Since some margin of error is possible in the assignment of 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of ziprasidone obtained using the methods described herein, over FIG. 2 and readily determine whether the X-ray diffraction pattern of the unidentified form is substantially the same as the X-ray powder diffraction pattern of the crystalline form of this invention. If the X-ray powder diffraction pattern is substantially the same as FIG. 2, the previously unknown crystalline form of ziprasidone can be readily and accurately identified as the crystalline form of this invention.

The invention also relates to a composition containing solid ziprasidone hydrochloride or solid ziprasidone, of which at least 80%, by total weight of the solid ziprasidone or its hydrochloride salt in the composition, is the corresponding crystalline form or an amorphous form. The invention also relates to the composition of solid ziprasidone hydrochloride comprising at least 80%, by total weight, the amorphous form of ziprasidone hydrochloride. In the more preferred form of this composition, the solid ziprasidone hydrochloride is suitable for use as active ingredient in formulating pharmaceutical products. The remainder of the solid ziprasidone hydrochloride in the composition, i.e., 20% or less of the total weight of ziprasidone hydrochloride, may be crystalline Form I of ziprasidone hydrochloride. In an embodiment of the invention, the composition may comprise at least 90% of the amorphous form of ziprasidone hydrochloride with respect to total weight of the solid ziprasidone hydrochloride in the composition. In another embodiment of the invention, the composition may comprise at least 95% of the amorphous form of ziprasidone hydrochloride with respect to total weight of the solid ziprasidone hydrochloride in the composition. In yet another embodiment of the invention, the composition is substantially free of any forms of ziprasidone hydrochloride other than its amorphous form.

The invention also relates to a composition of solid ziprasidone comprising at least 80%, by total weight of the crystalline of ziprasidone, which is set forth in this specification. The solid ziprasidone is suitable for use as active ingredient in formulating pharmaceutical products. In an embodiment of the invention, the composition may comprise at least 90% of the crystalline form of ziprasidone with respect to total weight of the solid ziprasidone in the composition. In another embodiment of the invention, the composition may comprise at least 95% of the crystalline form of ziprasidone with respect to total weight of the solid ziprasidone in the composition. In yet another embodiment of the invention, the composition is substantially free of any forms of ziprasidone other than its crystalline form.

X-ray diffraction provides a convenient and practical means for quantitative determination of the relative amounts of crystalline and/or amorphous forms in a solid mixture. X-ray diffraction is adaptable to quantitative applications because the intensities of the diffraction peaks of a given compound in a mixture are proportional to the fraction of the corresponding powder in the mixture. The percent composition of crystalline ziprasidone or its hydrochloride salt in an unknown composition can be determined. Preferably, the measurements are made on solid powder ziprasidone or it hydrochloride salt. The X-ray powder diffraction patterns of an unknown composition can be compared to known quantitative standards containing pure crystalline forms of ziprasidone or its hydrochloride salt to identify the percent ratio of a particular crystalline form. This is done by comparing the relative intensities of the peaks from the diffraction pattern of the unknown solid powder composition with a calibration curve derived from the X-ray diffraction patterns of pure known samples. The curve can be calibrated based on the X-ray powder diffraction pattern for the strongest peak from a pure sample of crystalline forms of ziprasidone or its hydrochloride salt. The calibration curve may be created in a manner known to those of skill in the art. For example, five or more artificial mixtures of crystalline forms of ziprasidone or its hydrochloride salt, at different amounts, may be prepared. In a non-limiting example, such mixtures may contain, 2%, 5%, 7%, 8%, and 10% of ziprasidone or its hydrochloride salt for each crystalline form. Then, X-ray diffraction patterns are obtained for each artificial mixture using standard X-ray diffraction techniques. Slight variations in peak positions, if any, may be accounted for by adjusting the location of the peak to be measured. The intensities of the selected characteristic peak(s) for each of the artificial mixtures are then plotted against the known weight percentages of the crystalline form. The resulting plot is a calibration curve that allows determination of the amount of the crystalline forms of ziprasidone or its hydrochloride salt in an unknown sample. For the unknown mixture of crystalline and amorphous forms of ziprasidone or its hydrochloride salt, the intensities of the selected characteristic peak(s) in the mixture, relative to an intensity of this peak in a calibration mixture, may be used to determine the percentage of the given crystalline form in the composition, with the remainder determined to be the amorphous material.

Pharmaceutical compositions comprising amorphous form of ziprasidone hydrochloride or the crystalline form of ziprasidone can be formulated with a one or more pharmaceutically acceptable carriers, also known as excipients, which ordinarily lack pharmaceutical activity, but have various useful properties which may, for example, enhance the stability, sterility, bioavailability, and ease of formulation of a pharmaceutical composition. These carriers are pharmaceutically acceptable, meaning that they are not harmful to humans or animals when taken appropriately and are compatible with the other ingredients in a given formulation. The carriers may be solid, semi-solid, or liquid, and may be formulated with the compound in bulk. The resulting mixture may be manufactured in the form of a unit-dose formulation (i.e., a physically discrete unit containing a specific amount of active ingredient) such as a tablet or capsule. The pharmaceutical compositions may include, in addition to a compound of this invention, one or more active pharmaceutical compounds.

Generally, the pharmaceutical compositions of the invention may be prepared by uniformly admixing the active ingredient with liquid or solid carriers and then shaping the product into the desired form. The pharmaceutical compositions may be in the form of suspensions, solutions, elixirs, aerosols, or solid dosage forms. Because of their ease of administration, tablets and capsules represent the most advantageous oral dosage unit form, in which case solid pharmaceutical carriers are employed.

A preferred oral solid preparation is a tablet. A tablet may be prepared by direct compression, wet granulation, or molding, of the active ingredient(s) with a carrier and other excipients in a manner known to those skilled in the art. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made on a suitable machine. A mixture of the powdered compound moistened with an inert liquid diluent is suitable in the case of oral solid dosage forms (e.g., powders, capsules, and tablets). If desired, tablets may be coated by standard techniques. The compounds of this invention may be formulated into typical disintegrating tablets, or into controlled or extended release dosage forms. Examples of suitable controlled release formulation vehicles are disclosed in U.S. Pat. Nos. 3,845,770; 3,916,899; 3,536,809; 3,598,123; and 4,008,719, incorporated herein by reference in their entireties.

The pharmaceutical compositions of the invention are contemplated in various formulations suitable for various modes of administration, including but not limited to inhalation, oral, rectal, parenteral (including subcutaneous, intradermal, intramuscular, intravenous), implantable, intravaginal and transdermal administration. The most suitable route of administration in any given case depends on the duration of the subject's condition, the length of treatment desired, the nature and severity of the condition being treated, and the particular formulation that is being used. The formulations may be in bulk or in unit dosage form.

The amount of active ingredient included in a unit dosage form depends on the type of formulation that is formulated. A pharmaceutical composition of the invention will generally comprise about 0.1% by weight to about 99% by weight of active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories, and tablets, each containing a pre-determined amount of the active compound; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers. The amount of active ingredient per unit dosage of solid formulations may be as described in prior art for preparations of ziprasidone and its hydrochloride salt. For liquid oral formulations, a preferable amount is from about 2% by weight to about 20% by weight. Suitable carriers include but are not limited to fillers, binders, lubricants, inert diluents, surface active/dispersing agents, flavorants, antioxidants, bulking and granulating agents, adsorbants, preservatives, emulsifiers, suspending and wetting agents, glidants, disintegrants, buffers and pH-adjusting agents, and colorants. Examples of carriers include celluloses, modified celluloses, cyclodextrins, starches, oils, polyols, sugar alcohols and sugars, and others. For liquid formulations sugar, sugar alcohols, ethanol, water, glycerol, and poyalkylene glycols are particularly suitable, and may also be used in solid formulations. Cyclodextrins may be particularly useful for increasing bioavailability. Formulations for oral administration may optionally include enteric coatings known in the art to prevent degradation of the formulation in the stomach and provide release of the drug in the small intestine.

Formulations suitable for buccal or sub-lingual administration include lozenges comprising the active compound in a flavored base, usually sucrose and acacia or tragacanth, although other agents are also suitable, and pastilles comprising the compound in an inert base such as gelatin and glycerin or sucrose and acacia.

Formulations suitable for rectal administration are preferably presented as unit dose suppositories. These may be prepared by admixing the active compound with one or more conventional solid carriers, e.g., cocoa butter, and then shaping the resulting mixture.

In another aspect, the invention also provides methods of treating a psychosis, comprising administering to a patient in need of such treatment an effective amount of a composition comprising the amorphous form of ziprasidone hydrochloride or the crystalline form of ziprasidone and a pharmaceutically acceptable carrier.

The effective amount (i.e., dosage) of active compound for treatment will vary depending on the route of administration, the condition being treated, its severity, and duration, and the state and age of the subject. A skilled physician will monitor the progress of the subject and will adjust the dosage accordingly, depending on whether the goal is to eliminate, alleviate, or prevent a given condition. Generally, the dosage should be considered in proportion to the subject's weight. The daily dose of particular formulations of active compound may be divided among one or several unit dose administrations. For example therapeutic administration about fifteen to thirty minutes before main meals is preferable (i.e. three times daily), although administration of the active compounds may be carried out prophylactically, and may be maintained for prolonged periods of time. One skilled in the art will take such factors into account when determining dosage. Unit dosage of active ingredient may range from about 0.1 to about 2 g or from about 0.1 to about 2 g.

The invention is further described by reference to the following examples which set forth in detail the preparation of compounds and compositions of the present invention, as well as their utility. It will be apparent to those skilled in the art, that many modifications, both to materials, and methods, may be practiced without departing from the purpose and interest of this invention. The examples that follow are not intended to limit the scope of the invention as described hereinabove or as claimed below.

REFERENCE EXAMPLE 1

Preparation of 5-(2-Chloro ethyl) -6-chloro oxindole

Triethylsilane (57.2 gm) was added slowly to the reaction mixture of 5-(2-Chloro acetyl) -6-chloro oxindole (50.0 gm) and trifluoroacetic acid (175 mL) below the temperature of 45° C. The reaction was maintained at 40-45° C. for 6 hours. The reaction mass was cooled to 0° C. to -5° C. and maintained stirring for 90 minutes. The separated solid was filtered and washed with water (50 mL). Then the wet compound was further slurred in water (250 mL) for 90 minutes. The resultant solid was filtered, washed with water (50 mL) and dried at a temperature of 70-75° C. to afford 5-(2-chloroethyl) -6-chloro oxindole (43.5 gm).

REFERENCE EXAMPLE 2

Preparation of Ziprasidone Base

Refluxed the reaction mixture of 5-(2-chloroethyl)-6-chloro oxindole (100 gm), 3-(1-piperazinyl)-1,2-benzisothiazole (104.7 gm), sodium carbonate (92.2 gm), sodium iodide (6.4 gm), tetra butyl ammonium bromide (28 gm) and cyclohexane (1000 mL) till the reaction was completed. The reaction mass was cooled to a temperature of 30° C. and the solid was filtered. To the wet compound was added water (1000 mL) and continued stirring for 45 minutes. The solid was filtered and washed with water (100 mL). To the water wet compound was added acetone (500 mL) and there was stirring for 2 hours at room temperature. The compound was filtered and washed with acetone (200 mL) and dried at a temperature of 70-75° C. to afford the Crude Ziprasidone base (156.9 g)

REFERENCE EXAMPLE 3

Preparation of Ziprasidone Base

Charged 5-(2-chloroethyl) -6-chloro oxindole (50 gm), 3-(1-piperazinyl)-1,2-benzisothiazole (47.5 gm) and cyclohexane (500 mL) into an autoclave. To this sodium carbonate (46 gm), sodium iodide (3.2 gm), tetra butyl phosphonium bromide (14.8 gm) was added and the reaction was maintained at a temperature of 95-102° C. and the pressure was kept at 2.5 kg/cm$^2$ till the reaction was completed. The reaction mass was cooled to 30° C. and water (250 mL) was added. The resulting compound was filtered and washed with water (100 mL). The wet compound was further slurred in water (500 mL), filtered and washed with water (100 mL). To the water wet compound was added acetone (500 mL) and was stirred at room temperature for 2 hours and 30 minutes. The solid was filtered, washed with acetone (100 mL) and dried at a temperature of 60-65° C. to afford the Ziprasidone base (65.7 gm).

EXAMPLE 1

Preparation of Amorphous Form of Ziprasidone Hydrochloride

Ziprasidone (5 g) and 50 mL of acetic acid were placed into a round bottom flask and heated to 45-50° C. Added was 25 mL of aqueous hydrochloric acid slowly to the mixture over 20 min. Then the reaction mixture was refluxed. Water (10 mL) was added, followed by addition of 50 mL of Isopropanol. The reaction mass was cooled to 50° C. and distilled off the solvent completely under vacuum. The material formed was scratched from the flask.

EXAMPLE 2

Preparation of Crystalline Form of Ziprasidone

Sodium carbonate (56.3 g) and 500 mL of water were placed into a round bottom flask. Added was 50 g of 3-(1-piperazinyl)-1,2-benzisothiazole hydrochloride and 50 g of 6-Chloro-5-(2-Chloroethyl) oxindole. The reaction mixture was then refluxed for 15 hours. The reaction completion was monitored by TLC. The reaction mass was cooled to room temperature. The resulting compound was filtered and washed with 50 mL of water. The wet compound and 250 mL of acetone were placed into a flask and the reaction mixture was stirred at room temperature for 2 hours. The reaction mixture was filtered to give a solid cake, which was washed with 50 mL of acetone. The wet cake and 750 mL of methanol were placed into a flask, which was heated to 50° C., and 14 mL of methane sulfonic acid was added to the solution over 20 minutes. The resulting reaction mass was cooled to room temperature and was subjected to a filtration to give a solid compound, which was washed with methanol. The wet compound and 750 mL of water were placed into a flask, and then pH of the solution was adjusted to pH 9 with caustic lye. The reaction mixture was then stirred at room temperature for 1 hour and filtered. The filtered compound was washed with water and dried at 70° C. to give 65 g of crystalline form Ziprasidone base.

The invention claimed is:

1. A process for making an amorphous form of ziprasidone hydrochloride, said process comprising:
   a. providing a ziprasidone hydrochloride solution in an aqueous alcoholic solvent;
   b. removing said solvent, thereby forming a solid mass; and
   c. isolating said solid mass, which is the amorphous form of ziprasidone hydrochloride.

2. The process of claim 1, wherein said aqueous alcoholic solvent is a mixture of water and an alcohol selected from the group consisting of ethanol, methanol, propanol, t-butanol, n-butanol, isopropanol, and mixtures thereof.

3. The process of claim 1, wherein said aqueous alcoholic solvent is a mixture of water and isopropyl alcohol.

4. The process of claim 1, wherein said ziprasidone hydrochloride solution is provided by a process comprising mixing ziprasidone in acetic acid with aqueous hydrochloric acid solution.

5. The process of claim 4, wherein said ziprasidone is a crystalline form, an amorphous form or a mixture thereof.

6. The process of claim 4, wherein said ziprasidone is a crystalline form.

7. The process of claim 4, wherein said ziprasidone is an amorphous form.

8. The process of claim 4, wherein said mixing is done at a temperature between about 30° C. and about 70° C.

9. The process of claim 4, wherein said mixing is done at a temperature between about 40° C. and about 50° C.

10. The process of claim 4, wherein said process for providing the ziprasidone hydrochloride solution further comprises heating to an elevated temperature.

11. The process of claim 4, wherein said process for providing the ziprasidone hydrochloride solution further comprises heating to reflux temperature.

12. The process of claim 1, wherein removing solvent occurs under reduced pressure.

* * * * *